(12) United States Patent
Voutilainen et al.

(10) Patent No.: US 10,337,978 B2
(45) Date of Patent: Jul. 2, 2019

(54) METHOD AND APPARATUS FOR DETERMINING THE LOCATION OF AN INTERFACE OF INTEREST, AND COMPUTER PROGRAM

(71) Applicant: ROCSOLE LTD, FI-Kuopio (FI)

(72) Inventors: Arto Voutilainen, Kuopio (FI); Pasi Laakkonen, Kuopio (FI); Anssi Lehikoinen, Kuopio (FI)

(73) Assignee: ROCSOLE LTD, Kuopio (FI)

( * ) Notice: Subject to any disclaimer, the term of this patent is extended or adjusted under 35 U.S.C. 154(b) by 840 days.

(21) Appl. No.: 14/763,635

(22) PCT Filed: Feb. 1, 2013

(86) PCT No.: PCT/FI2013/050113
§ 371 (c)(1),
(2) Date: Jul. 27, 2015

(87) PCT Pub. No.: WO2014/118425
PCT Pub. Date: Aug. 7, 2014

(65) Prior Publication Data
US 2015/0355126 A1  Dec. 10, 2015

(51) Int. Cl.
*G06F 17/10* (2006.01)
*G01N 17/00* (2006.01)
(Continued)

(52) U.S. Cl.
CPC ......... *G01N 17/008* (2013.01); *G01N 27/221* (2013.01); *G01N 27/226* (2013.01); *G01N 27/24* (2013.01)

(58) Field of Classification Search
None
See application file for complete search history.

(56) References Cited

U.S. PATENT DOCUMENTS 5,005,402 A    4/1991  Pischinger et al.
5,807,251 A    9/1998  Wang et al.
(Continued)

FOREIGN PATENT DOCUMENTS

JP    2009-156819 A    7/2009
JP    2012-208113 A    10/2012
RU    2428722 C2       9/2011

OTHER PUBLICATIONS

Darde et al. Fine Tuning Electrode Information in Electrical Impedance Tomography Inverse Problems and Imaging, Sep. 2012, pp. 1-22.*

(Continued)

*Primary Examiner* — Rehana Perveen
*Assistant Examiner* — Cuong V Luu
(74) *Attorney, Agent, or Firm* — Buchanan, Ingersoll & Rooney PC (57) ABSTRACT

A method for determining the location of an interface of interest in a target domain, between a free volume of a flowable material and a solid material limiting said free volume, the method involves the steps of providing a mathematical model of the target domain determining, for a plurality of pairs of electrode groups, a characteristic electrical quantity proportional to the capacitance of a capacitor formed by a pair of electrode groups; receiving measurements of the characteristic electrical quantity for a plurality of pairs of electrode groups; adjusting the mathematical model by varying the location of the boundary surface in order to take into account possible wear of the boundary surface so as to reduce the differences between the measured characteristic electrical quantities and those defined by the mathematical model; and determining the location of the interface of interest on the basis of the adjusted mathematical model.

15 Claims, 5 Drawing Sheets

(51) Int. Cl.
  *G01N 27/22* (2006.01)
  *G01N 27/24* (2006.01)

(56) References Cited

U.S. PATENT DOCUMENTS

| | | | |
|---|---|---|---|
| 6,501,266 | B1 | 12/2002 | Krivoi et al. |
| 7,496,450 | B2 | 2/2009 | Ortiz Aleman et al. |
| 8,762,084 | B2* | 6/2014 | Gao ............... G01N 27/228 702/65 |
| 8,823,396 | B2* | 9/2014 | Astley ............... G01R 27/02 324/660 |
| 2005/0167588 | A1* | 8/2005 | Donnangelo ........ A61B 5/0536 250/307 |
| 2007/0133746 | A1* | 6/2007 | Ortiz Aleman ........... G01F 1/64 378/59 |
| 2007/0186679 | A1* | 8/2007 | Zangl ............... G01F 1/64 73/861.18 |
| 2010/0097374 | A1* | 4/2010 | Fan ............... A61B 5/0535 345/420 |
| 2010/0213953 | A1* | 8/2010 | Yang ............... G01N 27/22 324/664 |
| 2011/0163770 | A1 | 7/2011 | Mahalingam et al. |
| 2012/0232810 | A1* | 9/2012 | Kaipio ............... G01N 27/06 702/45 |
| 2013/0085365 | A1* | 4/2013 | Marashdeh ............ A61B 5/05 600/386 |
| 2013/0214771 | A1* | 8/2013 | Tiernan ............... G01N 27/904 324/242 |
| 2015/0145532 | A1* | 5/2015 | Kersey ............... G01N 17/02 324/663 |

OTHER PUBLICATIONS

Hyvonen et al. Simultaneous Reconstruction of Outer Boundary Shape and Admittivity Distribution in Electrical Impedance Tomography arXiv:1205.3071v1, math.AP, May 14, 2012, pp. 1-21.*
Alme et al. Electrical Capacitance Tomography—Sensor Models, Design, Simulations, and Experimental Verification Meas. Sci. Technol. Nov. 2000, pp. 1256-1266.*
Jarworski et al. The Design of an Electrical Capacitance Tomography Sensor for Use With Media of High Dielectric Permittivity Meas. Sci. Technol. Nov. 2000, pp. 743-757.*
Hou et al. Electrical Impedance Tomographic Methods for Sensing Strain Fields and Crack Damage in Cementitious Structures Journal of Intelligent Material Systems and Structures, vol. 20, Jul. 2009, pp. 1363-1379.*
Quassai Marashdeh Advances in Electrical Capacitance Tomography Dissertation, The Ohio State University (Year: 2006).*
Wang et al. Electrical Capacitance Volume Tomography: Design and Applicatations Sensors 10, pp. 1890-1917 (Year: 2010).*
Xie et al. Electrical Capacitance Tomography for Flow Imaging: System Model for Development of Image Reconstruction Algorithms and Design of Primary Sensors IEE Proceedings-G, vol. 139, No. 1, Feb. 1992 (Year: 1992).*
Boyle et al.: "Shape Deformation in Two-Dimensional Electrical Impedance Tomography", IEEE Transactions on Medical Imaging, IEEE Service Center, Piscataway, NJ, US, vol. 31, No. 12, Dec. 1, 2012 (Dec. 1, 2012), pp. 2185-2193 (9 pages).
Nissinen et al.: "Reconstruction of Domain Boundary and Conductivity in Electrical Impedance Tomography Using the Approximation Error Approach", International Journal for Uncertainty Quantification, vol. 1, No. 3, Jan. 1, 2011 (Jan. 1, 2011 ), pp. 203-222 (20 pages).
International Search Report (PCT/ISA/210) dated Oct. 28, 2013, by the Finnish Patent Office as the International Searching Authority for International Application No. PCT/FI2013/050113.
A J Jaworski et al., "The Design of an Electrical Capacitance Tomography Sensor for Use With Media of High Dielectric Permittivity", Measurement Science and Technology, Jun. 2000, vol. 11, pp. 743-757, XP-020062959.
Office Action issued by the Russian Patent Office in corresponding Russian Patent Application No. 2015136863/28(056374) dated Jan. 18, 2017 (10 pages including partial English translation).
Nissinen et al.: "Compensation of Modelling Errors Due to Unknown Domain Boundary in Electrical Impedance Tomography," IEEE Transactions on Medical Imaging, Feb. 1, 2011, pp. 231-242, vol. 30, No. 2.
Darde et al.: "Fine-tuning electrode Information in electrical impedance tomography," Inverse Problems and Imaging, Sep. 1, 2012, pp. 391-421.
Extended European Search Report dated Oct. 4, 2016, by the European Patent Office in corresponding European Patent Application No. 13873954.5 (8 pages).

* cited by examiner

METHOD AND APPARATUS FOR DETERMINING THE LOCATION OF AN INTERFACE OF INTEREST, AND COMPUTER PROGRAM

FIELD OF THE INVENTION

The present invention relates generally to monitoring industrial processes where liquids or, in more general, any flowable materials flow or are stored in pipes, vessels, or containers. In particular, the present invention is related to solutions for monitoring scaling in and/or wear of the surfaces of such pipes, vessels, and containers.

BACKGROUND OF THE INVENTION

Contamination or so-called scaling is a well-known problem which may occur in many different applications in process industry. Scaling, often called also fouling, means generally deposition or accumulation of unwanted material on the surfaces of pipes, vessels, or other containers used for leading or storing flowable materials.

As a result of scaling, an extra layer of solid material is formed on such surface. Thereby, the free volume within the pipe or other container, open for the presence of a flowable material, is changed. This can lead to many problems. For example, changed shape of the free volume causes disturbances to the fluid flow. At least, the reduced cross-sectional area of the free inner volume of a process pipe increases the flow resistance through the pipe. In an extreme case, the pipe can be entirely clogged, thereby stopping the entire process at issue. In general, scaling is a common problem in various areas of process industry, causing significantly increased operational costs and production losses.

Material formed on the surfaces of process equipment by scaling must be removed from time to time. This can be very burdensome. Particularly when the extra material is formed by hydrocarbon bonding, it is typically very hard and extremely difficult to remove by mechanical processes. As an alternative to mechanical removal, different softening and releasing agents have been developed for various scaling materials. Instead of removing the formed scaling material afterwards, it is often more preferable to act proactively by preventing the scaling. For example, different chemicals can be used as scale inhibitors mixed with the flowable material to control the formation of inorganic hard scales. Use of such chemicals reduces the rate of scale formation and modifies the structure of the scale so that it is more easily removable. In any case, in order to prevent dramatic problems e.g. due to unexpected clogging of a process pipe, or to optimize the use of scale inhibitors, one should be able to monitor the scaling situation and its development in time.

On the other hand, another problem occurring in various industrial process equipment for leading and/or storing flowable materials is the wear of the walls of the pipelines and vessels. Wear may occur due to chemically aggressive materials reacting with the surfaces of the process equipment, but it can also result from simple mechanical abrasion caused e.g. by sand contained in a liquid flow. Similarly to scaling, also wear changes the volumes and flow conditions within the process equipment, and can thus affect adversely the processes. In an extreme case, wearing through of a wall of a pipeline or a vessel and the consequent sudden discharge of the flowable material to the exterior of the process equipment may result in severe accidents and high financial damages, and even injuries of persons. Similarly to scaling, also wear should thus be able to be monitored continuously.

Wear may also occur simultaneously with scaling. Therefore, it would be highly useful to have an efficient solution capable of on-line monitoring of those both phenomena.

In prior art, scaling and/or pipe wall wearing have been monitored or diagnosed e.g. with camera-based techniques, wherein a camera is installed in the process equipment to be analyzed, with acoustic (typically ultrasound) methods, or by simple mechanical methods in which special intelligent test objects are mounted onto the pipe walls. For example, EP 2115452 discloses as a specific example an apparatus and method for measuring scaling within a spiral wound membrane by transmitting acoustic signal into a tube, measuring the signal reflected from a material interface inside the tube, and comparing the measurement result with a reference signal from a known, clean tube.

The ultrasound and test object techniques are practically point measurements, limiting severely the applicability of the techniques. In camera-based techniques, the process must often be interrupted to perform the actual monitoring steps.

At the moment, there is no reliable on-line monitoring technique for detecting scaling and wear in an early stage. In particular, there is no efficient commercial solution available which could be used to monitor both of those harmful phenomena.

SUMMARY OF THE INVENTION

The purpose of the present invention is to provide an improved method, as well as an improved apparatus, for determining scaling and/or wear in industrial processes. It is also a purpose of the present invention to provide a novel a computer program product for performing said method.

The present invention is characterized by what is presented in claims 1, 8, and 15.

The present invention is focused on a method for determining the location of an interface of interest, which lies in a target domain, between a free volume of a flowable material and a solid material limiting said free volume. The industrial process where the interface of interest is to be localized may be any kind of process where scaling and/or wear may be present. These kinds of processes exist e.g. in oil production and refining, other oil based industries, and energy production, without limiting to these examples.

By "flowable material" is meant here any material which can flow in a process pipe or in a vessel or container. Such material can be in a liquid form but can also contain more or less solid or gaseous substance(s).

Examples of scale material in oil industry are bitumen and asphaltene, and various scaling materials covered by a common term "mineral scaling". The latter comprises e.g. calcium carbonate and calcium sulphate based compounds, the latter comprising e.g. gypsum. In energy production, scaling can occur e.g. due to the deposition of contaminants contained in water in surfaces of boilers. Water contaminants that can form boiler deposits include e.g. calcium, magnesium, iron, aluminum, and silica. The scale is typically formed as salts of these materials.

In the case of scaling formed in the target domain, the solid material limiting the free volume, and thus defining and limiting the interface of interest, may be the scale material. Other situations are discussed below.

The method of the present invention comprises the following steps.

First, the method comprises providing a mathematical model of the target domain determining, for a plurality of pairs of electrode groups, the electrodes of the electrode groups being arranged in capacitance measurement connection with the target domain and supported by a solid support body having a boundary surface in the target domain, a characteristic electrical quantity proportional to the capacitance of a capacitor formed by a pair of electrode groups.

The target domain referred to above means a two or three-dimensional area or volume under consideration in the method.

In general, the mathematical model means a numerical representation of the relationships between the physical material properties of the two or three-dimensional target domain and the characteristic electrical quantity. Thus, the general purpose of the mathematical model is to provide estimates of the values of the characteristic electrical quantity, which values are determined by the material properties in the target domain.

The characteristic electrical quantity can be any electrical quantity which is proportional to or dependent on the capacitance of a capacitor formed by a pair of electrode groups. The capacitance measurement connection between the electrodes and the target domain means that the electrodes are so connected to the target domain that capacitance measurements, or at least measurements of some characteristic electrical quantity proportional to the capacitance of capacitors formed by pairs of electrode groups, can be performed. To implement this, for example, there should not be any continuous electrically conductive body forming an equipotential shield between the electrodes and the target domain.

Being supported by the support body means that the electrodes may be mounted on any surface of the support body, or may be partly or entirely embedded within it so that they are possibly not in direct contact with the exterior of the support body. The selection of the most appropriate configuration depends, for example, on the material of the support body which may be formed of an electrically insulating or conductive material. In the first case, the electrodes may be embedded within the support body. In the case of an electrically conductive support body material, the electrodes should lie on a surface of the support body.

The boundary surface means here a surface of the support body defining an interface between the support body and the exterior thereof. Location "in" the target domain means that the boundary surface belongs to the two or three-dimensional target domain. In other words, this definition covers both situations where the boundary surface lies within the interior of the two or three-dimensional target domain, and situations where the boundary surface coincides with the target domain boundary, thus defining the boundary of the target domain.

An "electrode group" means here one or more of the electrodes. Thus, a capacitor under observation in the method can be formed between just a pair of two electrodes, but one or both of those single electrodes can also be replaced by a group of at least two separate electrodes.

The capacitance or some other capacitance dependent electrical quantity as the characteristic electrical quantity to be measured is based on the fact that the scale materials are typically electrically insulating materials, also in the cases where the flowable material itself may be electrically conductive.

The primary electrical quantity affecting the capacitance is naturally the electrical permittivity in the target domain. In other words, the capacitance, and thus any electrical quantity proportional to the capacitance of a capacitor formed between and by a pair of electrode groups, depend on the permittivity of the material(s) within the target domain. Conversely, in practice, the mathematical model preferably determines also the permittivity in the target domain. This can be determined as only one representative value, but more preferably as the permittivity distribution in target domain area or volume.

The method also comprises receiving measurements of the characteristic electrical quantity for a plurality of pairs of electrodes groups. "Receiving" means here that the method of the present invention itself does not necessarily comprise performing the actual measurements, but that such measurements, i.e. measured results, may be performed separately and just received as a step of the method. This allows, for example, an embodiment where the results of the measurements performed at a measuring site are sent electronically to an analysis site where the actual analysis and interface of interest determination is carried out. On the other hand, it is of course also possible to perform the measurements and analysis integrally, e.g. using a single analysis system comprising as well the electrodes and appropriate measurement equipment as computer means for performing the actual computations.

The measurements can be performed according to the principles as such well known in the field of electrical measurements, particularly in the field of electrical capacitance measurements. Further details and examples of possible characteristic electrical quantities determined by the mathematical model and measured by means of the pairs of electrode groups are discussed below in the detailed description section of this specification.

After having received the desired number of measured electrical quantity values, the mathematical model is adjusted so as to reduce the differences between the measured characteristic electrical quantity values and those determined by the mathematical model. This means comparing the measured electrical quantity values and the corresponding simulated values determined by the mathematical model, and changing the parameters of the mathematical model so that the simulated values becomes closer to the actual, measured ones so that the primary electrical quantity, e.g. the permittivity, has desired properties.

When sufficient consistency between the measured and the simulated electrical quantity values is achieved, the adjusted model representing the real target domain is used as a basis for determining the location of the interface of interest.

For example, when the model determines the permittivity distribution in the target domain, the adjusted model provides a reconstruction of the true permittivity distribution in the target domain, and the determination of the location of the interface of interest can be made on the basis of said permittivity distribution determined by the adjusted model. This is one preferred embodiment of the present invention. Abrupt changes in the reconstructed permittivity can be considered as indications of the presence of an interface between two materials, e.g. the flowable material in the free volume and the solid scale material deposited on the boundary surface. When the boundary surface lies within the interior of the target domain, such permittivity change can also indicate the location of the boundary surface of the support body itself. On the other hand, in the case of the boundary surface coinciding with the target domain border, non-existence of any clear permittivity change can be interpreted as no scale material having been formed on the boundary surface. Thus, to summarize, in the method of the present invention, the interface of interest can be as well the surface of a solid scale material as the boundary surface of the solid support body.

The link between the actual surfaces of process equipment under interest and the boundary surface is that the support body and the boundary surface thereof are considered simulating the true situation of scaling on and/or wear of those actual surfaces. For good correlation between the scale on and/or wear of the boundary surface, it is naturally preferable that the support body is formed of the same material as the actual process equipment. For example, in the case of monitoring scaling in a process pipe formed of a particular metal, also the support body is preferably formed of exactly the same metal composition. On the other hand, in the case of an electrically conductive support body, the electrodes need to be in a direct contact with the target domain. Thus, also the electrodes are then preferably formed of the same electrically conductive material as the pipe and the support body so that scale forms, and/or wear occurs on the electrodes similarly to the process pipe and the support body outside the electrodes.

In practice, the comparison of the measured and the corresponding simulated characteristic electrical quantity values, and changing the parameters of the mathematical model is generally known as an inverse problem or inverse calculation. Solving an inversion problem is based on typically rather complex computational algorithms performed at least partly automatically by means of suitable computation programs installed in a suitable processor. Several different algorithms suitable for the present invention are known in the art. Some of them are discussed in more detail in the detailed description section of this specification.

In general, the above process of providing a model of the target domain, making capacitance-related measurements, and adjusting the mathematical model so as to reduce the differences between the simulated and the measured electrical quantity values, may be called electrical capacitance tomography ECT. As one specific field within the more general electrical tomography, the principles, practical level implementation, and different variations of the ECT are well known in the art. In prior art, a typical example of utilization of ECT is imaging a multi-phase flow, wherein an image showing the areas or volumes of different phases within a material flow is generated. An example of this kind of method and different practical issues involved therein is discussed in U.S. Pat. No. 7,496,450 B2.

Thus, at the general level, the basic idea of the present invention concerns use of ECT to monitor scale and/or wear in industrial process equipment where flowable material is present. However, the method of the present invention is not necessarily true tomography in that a complete image showing the distribution of the electrical quantity of interest in the target domain is not necessarily generated. In some cases, the interface of interest can be determined on the basis of the adjusted mathematical model comprising, instead of complete electrical quantity distribution throughout the target domain, just some simplified representation of the target domain and the interface of interest therein.

As one very advantageous feature of the present invention, the above step of adjusting the mathematical model comprises varying the location of the boundary surface in order to take into account, in the step of determining the location of the interface of interest, possible wear of the boundary surface.

This feature is based on an observation by the inventors that in an ECT or ECT-like process applied to investigate the presence of possible scale deposit on the boundary surface, the estimates for the primary electrical quantity are very sensitive to inaccuracies in the geometry of the boundary surface. In other words, the inventors have found that already very small geometric mismodeling of the boundary surface may lead to large errors in the estimated permittivity distribution. In practice, this may be seen in erroneously determined presence of scale material on the boundary surface in a situation where, instead of any scale, the true boundary surface location has been changed as a result of wear thereof. In addition, the inventors have found that the effects of geometric mismodeling and the influence of the underlying permittivity distribution can be, to some extent, separated from each other meaning that possible changes in the boundary surface due to wear can be estimated together with the permittivity distribution. Therefore, the target domain shall be defined with a high accuracy. Irrespective of that, significant errors may occur if the boundary surface location is changed from the initial one. In practice, this may be seen in erroneously determined presence of a thickness of scale material on the boundary surface in a situation where, instead of any scale, the true boundary surface location has been changed as a result of wear thereof.

The principle in said varying of the boundary surface is that in addition to the actual parameterization related to the electrical quantity values, also the boundary surface location and/or geometry is varied in order to find the mathematical model best matching the measured results. In other words, both the parameterization of the shape of the boundary surface and the parameters determining the characteristic electrical quantity values are varied simultaneously. This efficiently reduces the possibility for error situations described above, and enables detection of the change of the boundary surface location as a result of wear. On the other hand, said detection of the true boundary surface location enables the use of the method also for applications, where the primary interest is not scaling but wear of the boundary surface, the presence of scale deposit possibly being a secondary object of interest or of no interest at all.

In the case of the boundary surface lying truly within the interior of the target domain, said varying of the location of the boundary surface comprises varying the geometry of the support body portion within the target domain. In the case where the boundary surface limits the target domain, said varying comprises varying the entire target domain geometry.

As known for those skilled in the field of electrical tomography, a mathematical model used as a numerical approximation of the target domain needs to be divided in pixels (two-dimensional case) or voxels (three-dimensional case), each representing the physical properties of the target domain at that particular location. The denser is this discretization the more detailed reconstruction of the target domain can be generated but, on the other hand, the more computational power is required to solve the inversion problem.

In a preferred embodiment of the present invention, to optimize the accuracy of the determination of the interface of interest location and thus the scale situation and/or wear of the boundary surface, a discretization having a varying density, the density increasing towards the boundary surface, is used. This can be implemented e.g. by selecting one dense discretization within a particular distance from the boundary surface, and another coarser discretization elsewhere. There can also be several different zones each having a differently arranged discretization. The density of the discretization can also vary continuously in the target domain.

The geometry of the support body supporting the electrodes for the measurements of the characteristic electrical quantity may vary depending on the application at issue. In one embodiment, the support body comprises a tubular body, the boundary surface being the inner surface of the tubular body. In this embodiment, the support body may be assembled as a part of a process pipe.

As another example of a suitable geometry and configuration, the support body may comprise a rod, the boundary surface being the surface of the rod. As yet another possible, the support body may comprise a plate-like body, the boundary surface being one of the two main surfaces of the plate-like body. By a main surface of a plate-like body is referred to a body having two substantially opposite surfaces, i.e. main surfaces, at a distance from each other, and one (e.g. in the case of a circular plate) or more side surfaces connecting the main surfaces, the main surfaces and the side surfaces defining the boundary of the three-dimensional body. These geometries allow very flexible placement of the support body and the electrodes in the process equipment. In one particular embodiment suitable for monitoring cylinder-symmetric processes, the electrodes can be arranged as a series of ring-like electrodes encircling the arm of the rod. With these kinds of electrodes, a three-dimensional inversion problem can be solved in two directions only: the axial direction along the axis of the rod, and the radial direction. This simplifies the calculations of a three dimensional system.

As already discussed above, the boundary surface may limit the target domain, i.e. define the boundary thereof. This approach is particularly useful for the cases where the support body is formed of an electrically conductive material, e.g. a metal. Metallic support body can be used in high temperatures and pressures, thus enabling using the ECT measurements in various harsh environmental conditions. Alternatively, the boundary surface may lie within the interior of the target domain so that the target domain extends behind the boundary surface. In this case, at least part of the support body thus is included in the target domain. This arrangement is suitable with the use of an electrically insulating support body.

In the above, the method has been described as being focused on the actual computational steps only. However, it is also in the scope of the present invention to perform a method further comprising providing a plurality of electrodes arranged in capacitance measurement connection with the target domain, the electrodes being supported by a solid support body having a boundary surface in the target domain, and measuring the characteristic electrical quantity for a plurality of pairs of electrode groups.

According to a device aspect, the principles of the present invention can also be implemented as an apparatus for determining the location of an interface of interest, in a target domain, between a free volume of a flowable material and a solid material limiting said free volume, the apparatus comprising at least one memory, and at least one processor coupled with the at least one memory; wherein the at least one memory comprises program code instructions, which when executed by the at least one processor, cause the apparatus to perform the steps described above in the context of the method aspect.

The at least one memory and the at least one processor may be implemented e.g. in the form of one or more computers, wherein suitable computer program code is installed for performing the method steps.

Similarly to the method, it is a very advantageous feature of the apparatus that the step of adjusting the mathematical model comprises varying the location of the boundary surface in order to take into account, in the step of determining the location of the interface of interest, possible wear of the boundary surface.

All what is stated about the advantages, details, and preferred features in the context of the method aspect of the present invention above are applicable, mutatis mutandis, also to the apparatus according to the present invention.

In the above, the apparatus according to the present invention is defined as comprising the computational means only. The device aspect of the present invention can also be implemented as a complete measurement system comprising, in addition to such apparatus, also a plurality of electrodes arranged in capacitance measurement connection with the target domain, the electrodes being supported by a solid support body having a boundary surface in the target domain, and a measurement apparatus configured to perform the measurements of the characteristic electrical quantity for a plurality of pairs of electrode groups.

Finally, the principles of the present invention can also be implemented in the form of a computer program comprising program code which, when executed by a processor, causes the processor to perform the method of as defined and described above.

BRIEF DESCRIPTION OF THE DRAWINGS

In the following, the present invention is described with reference to the accompanying drawings, wherein.

DETAILED DESCRIPTION OF THE EMBODIMENTS

Figure 1:
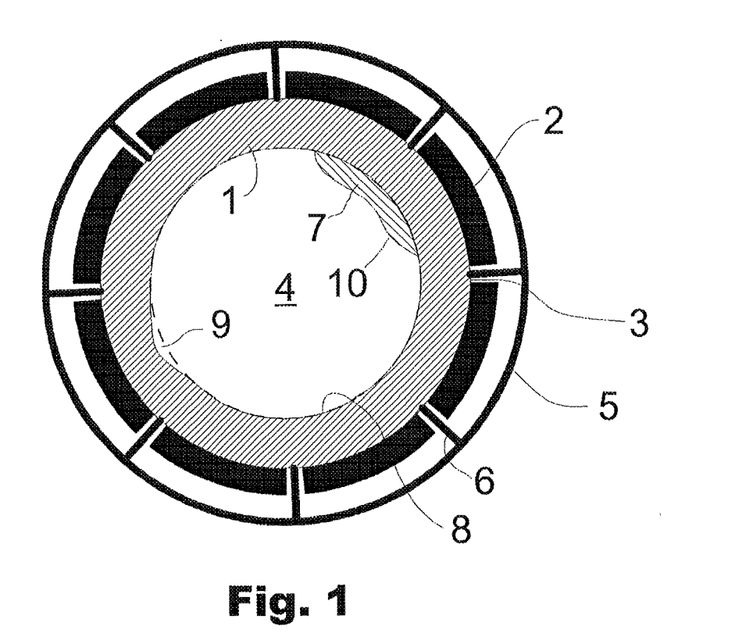
FIG. 1 shows a schematic cross-sectional view of an electrically insulating support body with an electrode arrangement.

FIG. 1 shows a schematic cross-sectional illustration of section of an electrically insulating pipe 1 forming a support body, on the outer surface of which eight electrodes 2 are attached for performing measurements of one or more capacitance-dependent electrical quantities in a target domain 3 comprising the inner volume 4 of the process pipe 1 as well as the pipe wall. Thus, in the example of FIG. 1, the boundary of the target domain 3 coincides with the outer surface of the pipe 1 and the inner surfaces of the electrodes 2 thereon. Alternatively, the electrodes could lie at least partly embedded in the pipe wall.

The electrically insulating pipe 1 is surrounded by a cylindrical metal sheath 5, comprising flanges 6 extending radially from the sheath to the outer surface of the pipe 1. For performing the measurements, the metal sheath and the flanges thereof are grounded (not illustrated in the drawing) and serve as a screen to isolate the system of the electrodes and the target domain from its surrounding and to prevent the electrodes from "seeing" each other directly via the exterior of the electrically insulating pipe. In the absence of such flanges, also the material(s) between the metal sheath 5 and outer surface of the pipe 1 would affect the capacitance-related measurements. In such case, the target domain should extend to the inner boundary of the metal sheath in order to take this effect into account in the calculations.

The inner volume 4 of the pipe 1 is filled with a process material flowing through the pipe. Scale material 7 in the form of solid deposit has been formed of the substances included in the flowing material on the pipe inner surface 8 forming a boundary surface of the pipe inner volume 4, thereby changing the free volume for the material flow. If continued, the scaling process can even clog the pipe entirely, thus preventing any flow through it.

As another change in comparison to the initial situation, the material of the electrically insulating pipe 1 has been eroded at one location of the pipe inner surface 8 so that a slight recess 9 has been formed thereon. Also the recess changes the flow conditions within the pipe 1. In addition to chancing the flow conditions, eroding can finally lead to breaking of the pipe as a result of wearing through of the pipe wall.

Figure 2:
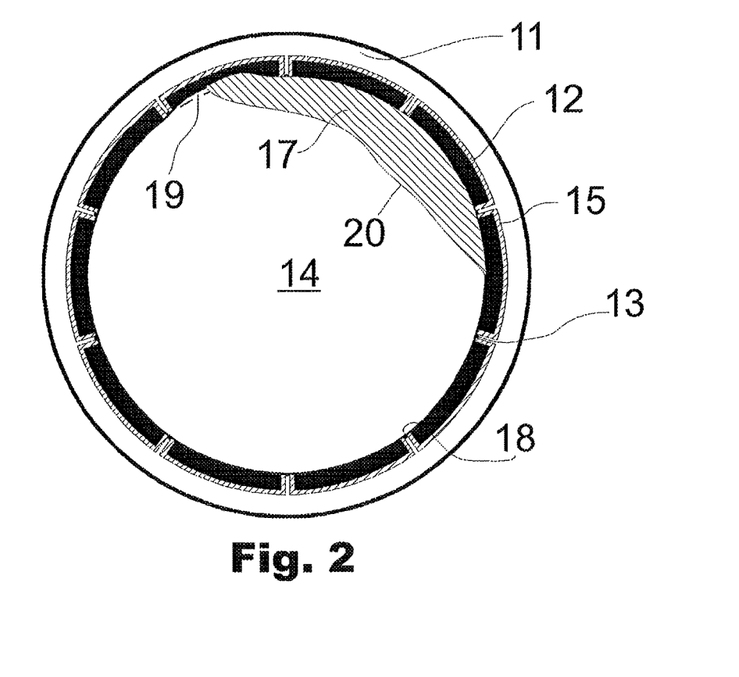
FIG. 2 shows a schematic cross-sectional view of an electrically conductive support body with an electrode arrangement.

An alternative example of a measurement setup enabling determination of scale and wear in a process pipe is shown in FIG. 2. As an essential difference in comparison to FIG. 1, there is an electrically conductive process pipe 11 formed e.g. of some metal. In the point of view of measuring capacitance-dependent electrical quantity values, an electrically conductive pipe necessitates the electrodes 12 being in a direct contact with the pipe inner volume 14. In this kind of situation, the target domain 13 in which the measurements are to be made is limited by the electrodes and the electrically conductive pipe inner surface 18 itself. Further, due to the electrically conductive material of the pipe 11, each electrode is electrically insulated from the pipe by means of thin electrically insulating 15 layer located between the electrode and the pipe wall.

Also in the situation of FIG. 2, there is scale 17 formed on the pipe inner surface 18, and a wearing process has eroded the pipe inner surface 18 and one of the electrodes forming a slight recess 19 thereon. Naturally, such recess could also extend to areas of more than one electrode only.

In FIGS. 1 and 2, eight and ten electrodes, respectively, have been installed on the pipes. However, these are just examples only, not limiting the applicability of the present invention to any number of electrodes suitably configured to allow measuring capacitances or other capacitance-dependent electrical quantities between the electrodes. Further, FIGS. 1 and 2 illustrate cross-sectional views of process pipes and one electrode ring only, thus referring to a two-dimensional target domain. However, it is possible to measure and monitor a three-dimensional target domain by arranging electrodes in several rings or layers along the axial direction of the process pipe.

In the following, determining the scale and wear within process equipment such as the pipes of FIGS. 1 and 2 is explained by reference to the flow chart of FIG. 3.

First, as an important step of the method, a mathematical model of the target domain is provided and stored e.g. in the memory of a computer. Mathematical model is built so as to comprise sufficient information to determine capacitances or some other capacitance-dependent electrical quantities between different electrode pairs or pairs of electrode groups. The information required for such determination can comprise e.g. the permittivity distribution within the target domain 3, 13. In practice, the model is a numerical representation of the physical target domain, the model including sufficient information about the material properties within the target domain so that estimates of the selected characteristic electrical quantity values to be measured by the electrodes can be determined on the basis of this information. The numerical model is divided into a plurality if discrete nodes or cells, each representing that particular location within the target domain. In the present invention, the most interesting zone within the target domain is the zone adjacent the process pipe inner surface 8, 18 forming a boundary surface of the free inner volume 4, 14 of the pipe. To enable sufficient accurate determination of scale and/or wear, the model is discretized more densely in the areas close to this boundary surface, and, in order to save computational power required, more coarsely in the centre of the pipe inner volume. An example of the geometry of a model 21, corresponding to the arrangement of FIG. 2 with ten electrodes, and the discretization thereof is illustrated in FIG. 4.

While the model gives an estimate of the true target domain and the selected physical quantity (quantities) describing the material(s) in the target domain, also information on the actual situation is required. This is realized by receiving, i.e. measuring or receiving readily-measured capacitances between groups of the electrodes 2, 12. By group of electrodes is meant one or more of the electrodes. For example, capacitance can be measured between a first group of just one electrode and another group comprising e.g. two, three, or more of the other electrodes.

The capacitance measurements can be performed according to the principles known in the art. In general, the field of ECT, the measurements are typically carried out as follows. Voltage supply (e.g. in square-wave, sinusoidal or triangular form) is applied to one of the electrodes (an excitation electrode) while the other electrodes are grounded. Capacitances between all electrode pairs are measured (in this example, each "group" of electrodes comprises just one single electrode). The capacitance measurement is repeated so that each of the electrodes is used as an excitation electrode. Therefore as a general rule, if there are N electrodes in the measurement system, $N*(N-1)/2$ independent capacitance values are obtained. Capacitances depend on the permittivity distribution in the target domain. Permittivity distribution of the target domain can then be estimated based on the set of the capacitance measurements. On the basis of the permittivity distribution, behaviour and/or some physical quantities of the underlying process can be investigated. Though capacitance is used as the electrical quantity to be measured in the exemplary process of FIG. 3 and the description above, it is important to note that any other electrical quantity which is proportional to capacitance, i.e. any capacitance-dependent electrical quantity, can also be selected to be used in the measurements and in the calculations.

For example, measuring a capacitance means usually supplying a voltage to charge the capacitor, and measuring the current when the capacitor is discharged. In practice, the permittivity of a material is generally a complex valued quantity, thus having both a real and an imaginary portion. When observed in AC conditions, a complex permittivity of a material affects both the amplitude and the phase of the discharge current. Measuring only the amplitude gives information on the real part of the permittivity only, whereas the phase information links the measurement to the complex portion of the permittivity. As an alternate to the complex permittivity, one could also talk about complex capacitance. As an interesting issue, if both the phase and amplitude information of the supplied and measured signals are taken into consideration, also the electrical conductivity distribution within the target domain can possibly be estimated.

When phase information is to be measured, sinusoidal supply voltage is preferably used.

When the required measurements are received, the capacitances or other capacitance-dependent electrical quantity values determined by the model are compared with the measured results, and the model, i.e. its parameters, is adjusted so that the difference between the modelled and measured values is decreased. The goal is to find a permittivity distribution within the target domain for which the numerical model outcome corresponds closely to the measurements. In this comparison and adjustment, principles and algorithms as such known in the field of ECT and inversion mathematics can be used. For example, when generating a complete reconstruction of the permittivity distribution within the target domain, image reconstruction algorithms may generally be non-iterative or iterative algorithms. Among the first algorithm group, one simple and fast algorithm is the Linear Back-Projection (LBP) algorithm. In the LBP method, the relationship between the capacitance and permittivity distribution can be approximated in a linear normalized form as:

$$B = S \cdot X \quad (1)$$

where B is a normalized capacitance vector, S is a transducer sensitivity matrix (normalized capacitance with respect to normalized permittivity), and X is a normalized permittivity vector. The task in the analysis is to find out X, while B is known and S is predetermined as desired.

It should be noted that the permittivity of the pipe wall can be regarded as an unknown parameter to be estimated but usually its geometry and permittivity value are at least approximately known and this information can be used in the image reconstruction.

As an essential feature, in the step of adjusting the mathematical model, the location of the boundary surface is varied. The purpose of this varying is to take into account the possible wear of the boundary surface, i.e. the change of its location. Thus, the principle is to parameterize the boundary of interest and estimate the boundary parameters simultaneously with the actual permittivity distribution. This approach relies on the observation by the inventors that both the geometry of and permittivity in the target domain affect the ECT measurements and their effects are (at least to some degree) orthogonal to each other. The varying and estimation of the target domain shape parameters and the permittivity distribution may be based on a Bayesian inversion approach in which a statistical model is constructed for the effects due to the variations in geometry. In the following, this is discussed in more detail.

In general, the key step in the ECT image reconstruction comprises building a feasible numerical model of the system under inspection. The model gives the relations between the permittivity distribution and the mutual capacitances of the electrode configuration. With the aid of this model, the goal is to determine an estimate for the permittivity distribution so that the modeled capacitances are in close agreement with measured ones. In the Bayesian inversion approach the permittivity distribution and observed data are modeled as random variables, and the objective is to determine the probability density function of the permittivity distribution conditioned over the measurements. Measurements do not usually provide sufficient information so that a unique solution would exist; therefore, it is necessary to employ appropriate prior densities for $\varepsilon(x)$. In the scaling and wearing determination, the objective is to determine the location of the interface of interest, i.e. the boundary of the scale or the boundary surface of the support body, and thus it is appropriate to employ prior models that preserve the edges that exist in the actual permittivity distribution. Examples of suitable non-parametric "edge-preserving" prior models are the total variation prior and specially designed Gaussian prior. Depending on the application and the target to be imaged, it can be advantageous to use parametric models to describe the target. The parametric model is chosen so that it can describe rapid spatial changes in the permittivity distribution.

Statistical properties of the measurement noise affect the quality of the reconstructed images, and with the Bayesian approach the statistics of the measurement noise can be modeled and accounted for in computations. The numerical model needed in the ECT imaging is an approximation of the actual behavior of the measurement system. At least the model suffers from inaccuracies due to numerical approximation of the governing continuous mathematical model. In addition, the system modeling may be challenging because the geometry is not usually perfectly known due to mechanical tolerances of the manufacturing. Furthermore, small changes in external measurement conditions (resulting e.g. to dimension changes due to thermal expansion) may lead to additional errors in the estimated permittivity distributions since their effects are not directly related to the used model. The effects of these types of modeling uncertainties can be, to some extent, compensated using an approximation error approach in which a statistical model is constructed for the effects of the model uncertainties using numerical simulations. Bayesian inversion approach is a natural framework for incorporating information on model errors into image reconstruction.

The goal in the Bayesian inversion is to determine the probability density function of the primal quantity conditioned over observations. In practical applications, it is usually necessary to determine some point estimates to give a concrete view of the situation on the ECT sensor. The computation of point estimates typically leads to optimization problems which are solved using the Newton's method or the Gauss-Newton method. Alternatively, another popular point estimate is the (conditional) expected value which is usually sought using sampling-based integration methods such as the Markov Chain Monte Carlo methods.

After adjusting the mathematical model so that a sufficient consistency between the measurements and the model exists, the location of the interface of interest in the target domain, i.e. the boundary surface 8, 18 or the surface 10, 20 of a scale material 7, 17 thereon is determined on the basis of the adjusted model. In practice, this is typically determined on the basis of some discontinuities in the values of the electrical quantities determined by the model, such as the permittivity. The lack of any such discontinuity results in determination of the boundary surface as the interface of interest. This kind of situation is an indication of no scale on the boundary surface.

The support body, such as the pipes 1, 11 of FIGS. 1 and 2 do not necessarily belong to the actual process equipment to be monitored, but may be provided in the form of a separate measurement probe located in the process equipment. In order to ensure sufficiently similar behavior of the support body and the actual process equipment itself, and thus the reliability of the scale/wear determination on the basis of monitoring scale on and/or wear of the support body, the support body is preferably formed of the same material as the actual process equipment.

Figure 3:
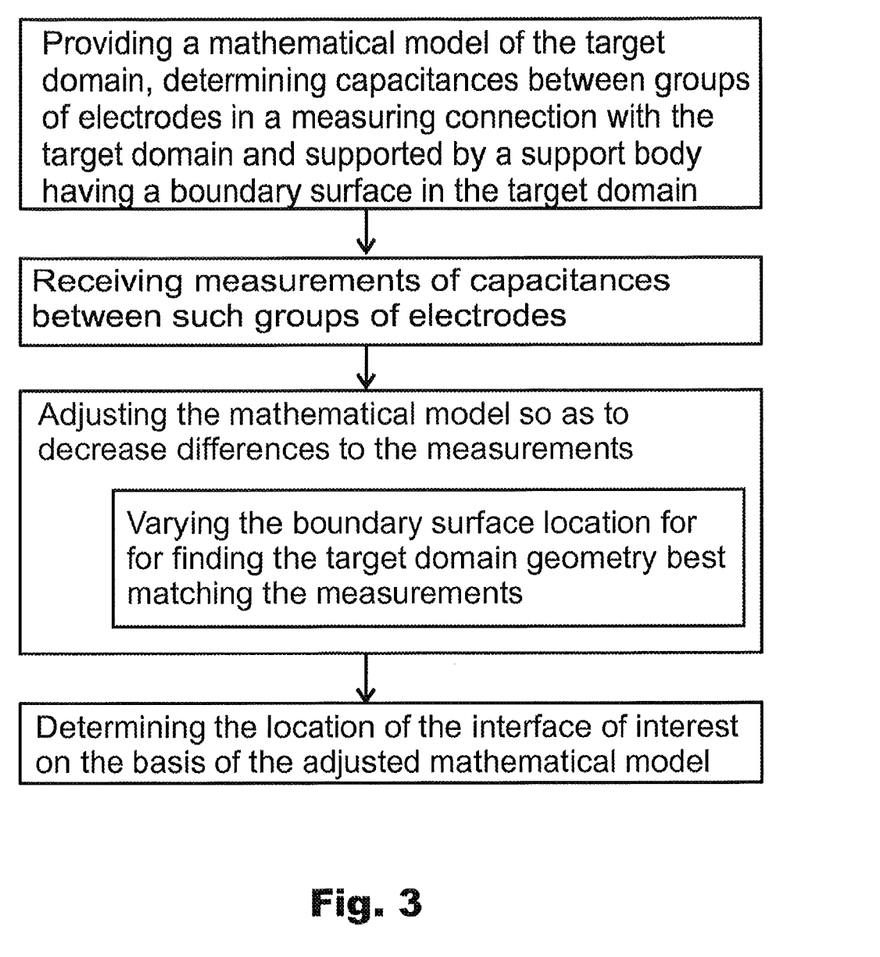
FIG. 3 is a flow chart illustration of a method for determining scaling and/or wear in process equipment.
Figure 4:
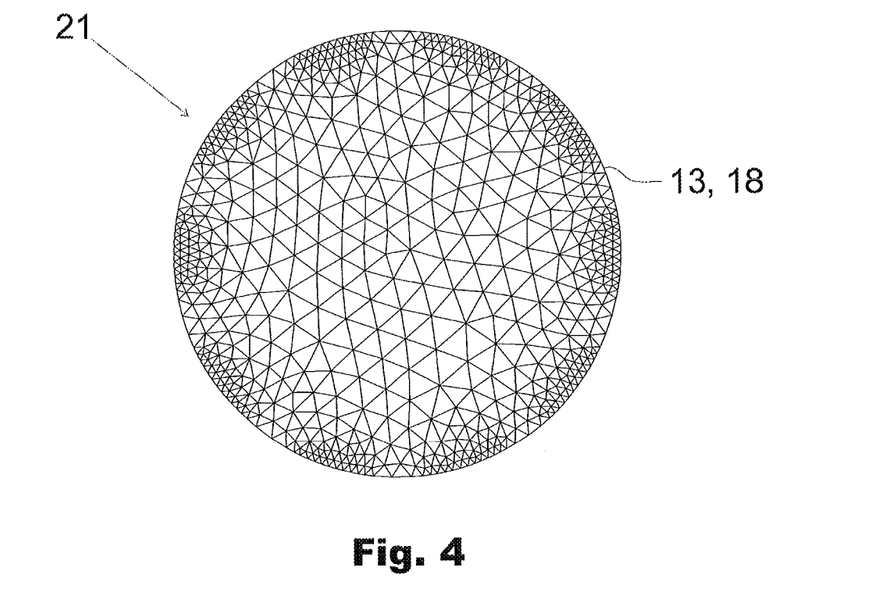
FIG. 4 shows an example of discretization of a target domain in a mathematical model representing the target domain.

To summarize, the method illustrated in FIG. 3 provides a reliable way to determine the presence of scale and/or wear in process equipment. Also the rate of scaling and/or wear can be determined when the inversion problem is solved over time by using sequential measurements.

Figure 5:
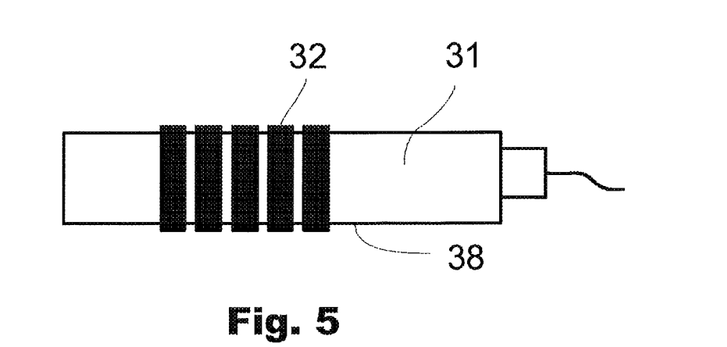
FIG. 5 shows a schematic side view of another type of support body with an electrode arrangement.

In cases where scaling or wear in a process can be assumed to be uniform (e.g. when the scale material deposits uniformly onto the walls of a pipe or a vessel walls), it is possible to reduce the computational cost of the method by taking advantage of symmetry. FIG. 5 shows a rod 31 forming a support body, and an electrode configuration wherein a plurality of ring electrodes 32 is mounted on the surface 38 of the rod-shaped support body. Potential fields generated by ring-like electrodes are cylinder-symmetric. Thus, a Finite Element Method (FEM) approximation used to model the target domain can be formulated in two dimensions (axial and radial) only, which reduces the computational complexity remarkably.

Figure 6:
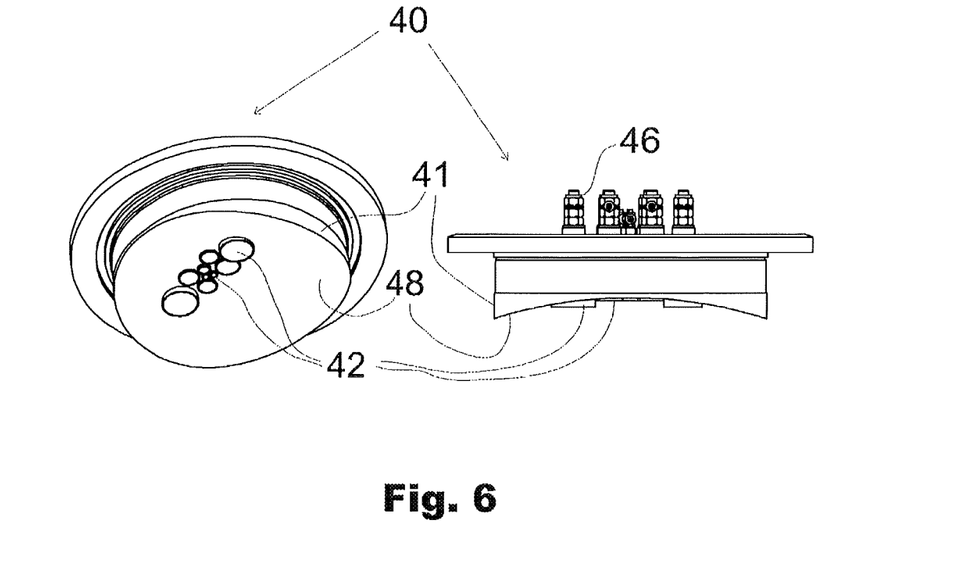
FIG. 6 shows yet another type of support body with an electrode arrangement.

As yet another alternative, the support body can be formed as a simple plate-like body 41, as is the case in the measurement probe 40 shown in FIG. 6. The exemplary measurement probe 40 of FIG. 6 is configured to be installed through a wall of a cylindrical vessel so that the actual support body 41, having a plurality of electrodes 42 thereon, faces towards the interior of the vessel. The backside of the measurement probe comprises connectors 46 for connecting the electrodes 42 to appropriate measurement electronics. In the example of FIG. 6, there are electrodes 42 with different sizes.

The boundary surface 48 of the support body is shaped curved so as to coincide with the inner surface of the wall of the cylindrical vessel. Naturally, the boundary surface of a plate-like support body could also be planar or have some other non-planar shape than the curved one shown in FIG. 6. Also, it is to be noted that the thickness of a "plate-like" support body can vary according to the conditions of the actual application at issue.

Figure 7:
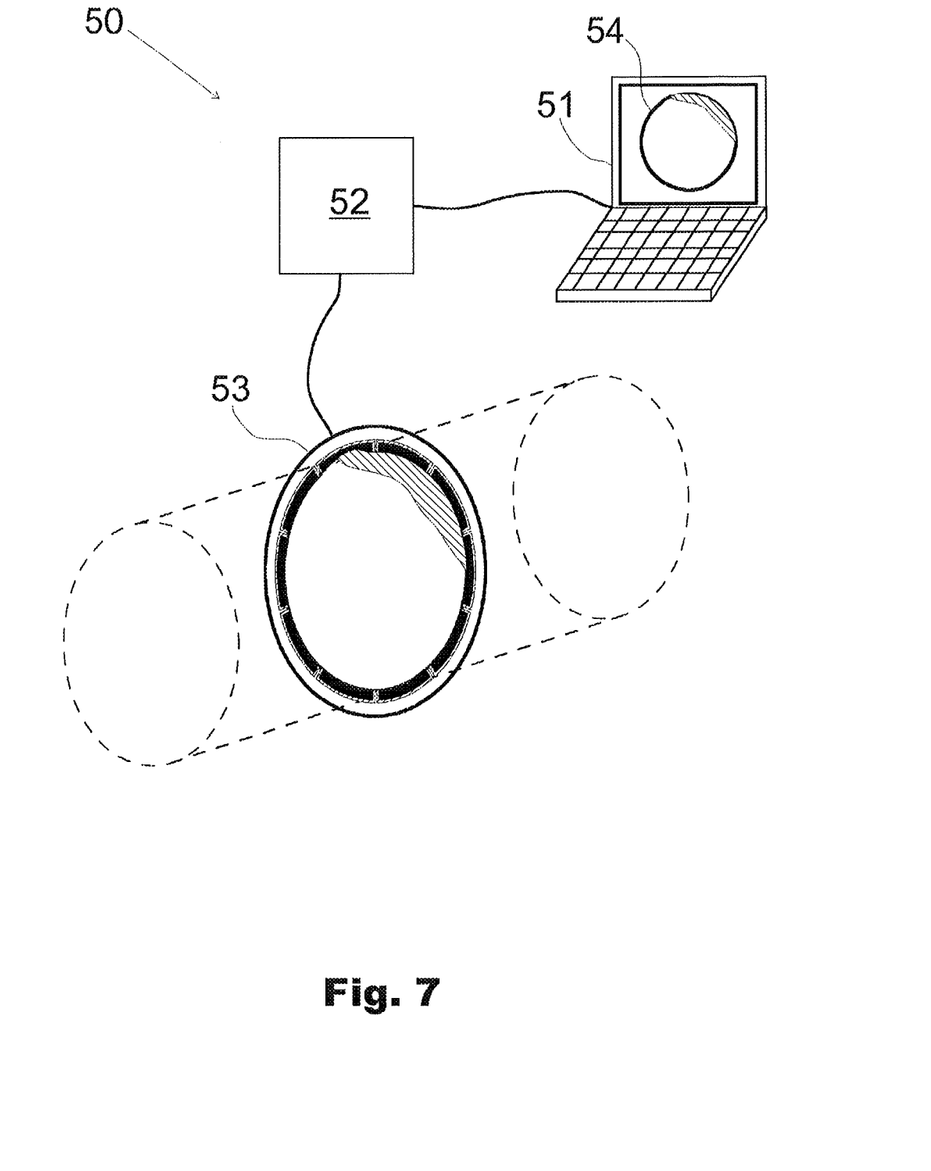
FIG. 7 shows an example of a system for determining scaling and/or wear in process equipment.

FIG. 7 illustrates schematically a system 50 by which the method as described above can be carried out. In the operational core of system, there is a computer 51 comprising an appropriate number of memory circuits and processors for storing the mathematical model and performing the computational steps of the method. The system further comprises a measurement electronics unit 52 and a measurement probe 53 comprising an annular support body and a plurality of electrodes. The support body and the electrodes can be configured e.g. according to those illustrated in FIG. 2. The measurement electronics unit is connected to the computer so that the measurement electronics unit can be controlled by the computer and that the measurement results can be sent to and received by the computer for further processing. The computer comprises a program code configured to control the computer to carry out the steps of the method as described above. As a result of the method performed by the system, an image 54 of the target domain is generated on the basis of the reconstructed permittivity distribution within the target domain inside the annular support body of the measurement probe 53. The image shows the scale on and the wear of the support body boundary surface.

It is obvious to a person skilled in the art that with the advancement of technology, the basic idea of the invention may be implemented in various ways. The invention and its embodiments are thus not limited to the examples described above; instead they may freely vary within the scope of the claims.

The invention claimed is:

1. A method for determining the location of an interface of interest, in a target domain, between a free volume of a flowable material and a solid material limiting said free volume, the method comprising the steps of:
providing a mathematical model of the target domain determining, for a plurality of pairs of electrode groups, the electrodes of the electrode groups being arranged in capacitance measurement connection with the target domain and supported by a solid support body having a boundary surface in the target domain, a characteristic electrical quantity proportional to the capacitance of a capacitor formed by a pair of electrode groups;
receiving measurements of the characteristic electrical quantity for a plurality of pairs of electrode groups;
adjusting the mathematical model so as to reduce the differences between the measured characteristic electrical quantity values and those determined by the mathematical model; and
determining the location of the interface of interest between the free volume of the flowable material and the solid material limiting said free volume on the basis of the adjusted mathematical model;
wherein the step of adjusting the mathematical model comprises varying the location of the boundary surface in order to take into account, in determining the location of the interface of interest between the free volume of the flowable material and the solid material limiting said free volume, wear of the boundary surface.

2. A method as defined in claim 1, wherein the mathematical model is discretized into a plurality of discrete elements each representing one discrete location, the discretization having a varying density, the density increasing towards the boundary surface.

3. A method as defined in claim 1, wherein the support body comprises a tubular body, the boundary surface being the inner surface of the tubular body.

4. A method as defined in claim 1, wherein the support body comprises a rod, the boundary surface being the surface of the rod.

5. A method as defined in claim 1, wherein the support body comprises a plate-like body, the boundary surface being one of the two main surfaces of the plate-like body.

6. A method as defined in claim 1, wherein the boundary surface limits the target domain.

7. A method as defined in claim 1, wherein the boundary surface lies within the interior of the target domain.

8. An apparatus for determining the location of an interface of interest, in a target domain, between a free volume of a flowable material and a solid material limiting said free volume, the apparatus comprising at least one memory, and at least one processor coupled with the at least one memory; wherein the at least one memory comprises program code instructions, which when executed by the at least one processor, cause the apparatus to perform the following steps:
providing a mathematical model of the target domain determining, for a plurality of pairs of electrode groups, the electrodes of the electrode groups being arranged in capacitance measurement connection with the target domain and supported by a solid support body having a boundary surface in the target domain, a characteristic electrical quantity proportional to the capacitance of a capacitor formed by a pair of electrode groups;
receiving measurements of the characteristic electrical quantity for a plurality of pairs of electrode groups;
adjusting the mathematical model so as to reduce the differences between the measured characteristic electrical quantity values and those determined by the mathematical model; and determining the location of the interface of interest between the free volume of the flowable material and the solid material limiting said free volume on the basis of the adjusted mathematical model;

wherein the step of adjusting the mathematical model comprises varying the location of the boundary surface in order to take into account, in determining the location of the interface of interest between the free volume of the flowable material and the solid material limiting said free volume, wear of the boundary surface.

9. An apparatus as defined in claim 8, wherein the mathematical model is discretized into a plurality of discrete elements each representing one discrete location, the discretization having a varying density, the density increasing towards the boundary surface.

10. An apparatus as defined in claim 8, wherein the support body comprises a tubular body, the boundary surface being the inner surface of the tubular body.

11. An apparatus as defined in claim 8, wherein the support body comprises a rod, the boundary surface being the surface of the rod.

12. An apparatus as defined in claim 8, wherein the support body comprises a plate-like body, the boundary surface being one of the two main surfaces of the plate-like body.

13. An apparatus as defined in claim 8, wherein the boundary surface limits the target domain.

14. An apparatus as defined in claim 8, wherein the boundary surface lies within the interior of the target domain.

15. A non-transitory computer-readable medium encoded with program code which, when executed by a processor, causes the processor to perform the method of claim 1.

* * * * *